(12) United States Patent
Fish et al.

(10) Patent No.: US 7,794,737 B2
(45) Date of Patent: *Sep. 14, 2010

(54) ODOR ABSORBING EXTRUDATES

(75) Inventors: Jeffrey Eldon Fish, Dacula, GA (US); Sharon Linda Greene, Canton, GA (US); John Gavin MacDonald, Decatur, GA (US); Jaeho Kim, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1201 days.

This patent is subject to a terminal disclaimer.

(21) Appl. No.: 10/687,425

(22) Filed: Oct. 16, 2003

(65) Prior Publication Data

US 2010/0211034 A1    Aug. 19, 2010

(51) Int. Cl.
*A61K 9/00* (2006.01)
*A61K 9/14* (2006.01)
*A01N 25/34* (2006.01)
*A01N 59/20* (2006.01)
*A61L 9/00* (2006.01)
*D04H 1/46* (2006.01)
*B32B 5/26* (2006.01)
*B32B 27/12* (2006.01)

(52) U.S. Cl. .................. 424/400; 424/402; 424/76.1; 424/489; 424/630; 422/5; 442/402; 442/381; 442/394

(58) Field of Classification Search .............. 424/400, 424/76.1, 489, 630, 402; 422/5; 442/402, 442/381, 394; 977/773, 904
See application file for complete search history.

(56) References Cited

U.S. PATENT DOCUMENTS

| | | |
|---|---|---|
| 2,015,864 A | 10/1935 | Müller et al. |
| 2,593,146 A | 4/1952 | Howard |
| 3,266,973 A | 8/1966 | Crowley |
| 3,338,992 A | 8/1967 | Kinney |
| 3,341,394 A | 9/1967 | Kinney |
| 3,381,688 A | 5/1968 | Satas |
| 3,494,821 A | 2/1970 | Evans |
| 3,502,538 A | 3/1970 | Petersen |
| 3,502,763 A | 3/1970 | Hartmann |
| 3,507,269 A | 4/1970 | Berry |
| 3,542,615 A | 11/1970 | Dobo et al. |
| 3,615,478 A | 10/1971 | Hoshino et al. |
| 3,692,618 A | 9/1972 | Dorschner et al. |
| 3,794,497 A | 2/1974 | Pratt et al. |
| 3,802,817 A | 4/1974 | Matsuki et al. |
| 3,849,241 A | 11/1974 | Butin et al. |
| 3,919,437 A | 11/1975 | Brown et al. |
| 3,960,494 A | 6/1976 | Verma et al. |
| 3,971,665 A | 7/1976 | Suzuki et al. |
| 4,006,030 A | 2/1977 | Yoshida et al. |
| 4,041,203 A | 8/1977 | Brock et al. |
| 4,078,029 A | 3/1978 | Yoshida et al. |
| 4,100,324 A | 7/1978 | Anderson et al. |
| 4,101,638 A | 7/1978 | Inoue et al. |
| 4,144,370 A | 3/1979 | Boulton |
| 4,172,781 A | 10/1979 | Walk et al. |
| RE30,797 E | 11/1981 | Davis |
| RE30,803 E | 11/1981 | Davis |
| 4,313,820 A | 2/1982 | Farha, Jr. et al. |
| 4,340,563 A | 7/1982 | Appel et al. |
| 4,375,448 A | 3/1983 | Appel et al. |
| 4,407,960 A | 10/1983 | Tratnyek |
| 4,467,012 A | 8/1984 | Pedersen et al. |

(Continued)

FOREIGN PATENT DOCUMENTS

| | | |
|---|---|---|
| EP | 0103214 | 3/1984 |
| EP | 0232141 | 8/1987 |
| EP | 0251783 | 1/1988 |
| EP | 0339461 | 11/1989 |
| EP | 0348978 A2 | 1/1990 |
| EP | 0376448 | 7/1990 |
| EP | 0389015 | 9/1990 |
| EP | 0389023 | 9/1990 |
| EP | 0483500 A1 | 5/1992 |
| EP | 0510619 A1 | 10/1992 |

(Continued)

OTHER PUBLICATIONS

Edwards et al., Microscale purification systems for biological sample preparation, Biomedical Microdevices 3:3, 211-218, 2001.*
Reyerson et al. (The electrokinetic potentials of precipitates, J. Phys. Chem., 1947, 51 (1), pp. 321-332).*
Abstract of Japanese Patent No. JP04255767, Sep. 10, 1992.
Abstract of Japanese Patent No. JP05098185, Apr. 20, 1993.
U.S. Appl. No. 10/723,761, filed Nov. 26, 2004, Quincy, III, et al., Odor Control In Personal Care Products.
U.S. Appl. No. 10/955,316, filed Sep. 30, 2004, MacDonald, et al., Odor-Reducing Quinone Compounds.

(Continued)

*Primary Examiner*—Robert A Wax
*Assistant Examiner*—Aradhana Sasan
(74) *Attorney, Agent, or Firm*—Dority & Manning, P.A.

(57) ABSTRACT

This invention concerns extrudates having high surface area materials and at least one metal ion adsorbed onto the high surface area material. The extrudates may be breathable films, multilayer laminates and pultruded articles. The extrudates may be made into storage and packaging material to reduce odor and retard the ripening of fruit. The extrudates, if in the form of a breathable film or multilayer laminate may be used as outer cover material for personal care products like diapers, adult incontinence products, training pants and the like. The high surface area particle-containing extrudate may be made by adding modified nanoparticles to a filler before the filler is treated with a fatty acid. Alternatively, a filler previously treated with a fatty acid may be modified by subjecting the filler to sonic energy in the presence of an aqueous solution of metal ions and nanoparticles.

29 Claims, 4 Drawing Sheets

U.S. PATENT DOCUMENTS

| | | | |
|---|---|---|---|
| 4,469,746 A | 9/1984 | Weisman et al. |
| 4,488,969 A | 12/1984 | Hou |
| 4,494,278 A | 1/1985 | Kroyer et al. |
| 4,494,629 A | 1/1985 | Raeburn |
| 4,517,308 A | 5/1985 | Ehlenz et al. |
| 4,522,203 A | 6/1985 | Mays |
| 4,525,410 A | 6/1985 | Hagiwara et al. |
| 4,575,556 A | 3/1986 | Byrne et al. |
| 4,604,313 A | 8/1986 | McFarland et al. |
| 4,640,810 A | 2/1987 | Laursen et al. |
| 4,643,801 A | 2/1987 | Johnson |
| 4,655,757 A | 4/1987 | McFarland et al. |
| 4,701,218 A | 10/1987 | Barker et al. |
| 4,715,983 A | 12/1987 | Ota et al. |
| 4,725,415 A | 2/1988 | Kidd |
| 4,734,324 A | 3/1988 | Hill |
| RE32,649 E | 4/1988 | Brandt et al. |
| 4,775,585 A | 10/1988 | Hagiwara et al. |
| 4,780,448 A | 10/1988 | Broecker et al. |
| 4,781,858 A | 11/1988 | Mizukami et al. |
| 4,783,220 A | 11/1988 | Gamble et al. |
| 4,798,603 A | 1/1989 | Meyer et al. |
| 4,802,473 A | 2/1989 | Hubbard et al. |
| 4,818,464 A | 4/1989 | Lau |
| 4,823,404 A | 4/1989 | Morell et al. |
| 4,823,803 A | 4/1989 | Nakamura |
| 4,904,304 A | 2/1990 | Watanabe et al. |
| 4,969,457 A | 11/1990 | Hubbard et al. |
| 4,978,615 A | 12/1990 | Aoyama et al. |
| 4,988,505 A | 1/1991 | Watanabe et al. |
| 5,000,746 A | 3/1991 | Meiss |
| 5,020,533 A | 6/1991 | Hubbard et al. |
| 5,057,302 A | 10/1991 | Johnson et al. |
| 5,064,473 A | 11/1991 | Kubo et al. |
| 5,100,581 A | 3/1992 | Watanabe et al. |
| 5,100,702 A | 3/1992 | Maeda et al. |
| 5,108,739 A | 4/1992 | Kurihara et al. |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,196,177 A | 3/1993 | Watanabe et al. |
| 5,204,429 A | 4/1993 | Kaminsky et al. |
| 5,209,998 A | 5/1993 | Kavassalis et al. |
| 5,220,000 A | 6/1993 | Theodoropulos |
| 5,221,497 A | 6/1993 | Watanabe et al. |
| 5,225,374 A | 7/1993 | Fare et al. |
| 5,230,953 A | 7/1993 | Tsugeno et al. |
| 5,238,518 A | 8/1993 | Okubi et al. |
| 5,245,117 A | 9/1993 | Withers et al. |
| 5,266,289 A | 11/1993 | Tsugeno et al. |
| 5,284,703 A | 2/1994 | Everhart et al. |
| 5,292,868 A | 3/1994 | Subramanian |
| 5,294,717 A | 3/1994 | Theodoropulos |
| 5,300,365 A | 4/1994 | Ogale |
| 5,314,855 A | 5/1994 | Thorpe et al. |
| 5,322,061 A | 6/1994 | Brunson |
| 5,332,432 A | 7/1994 | Okubi et al. |
| 5,338,713 A | 8/1994 | Takagi et al. |
| 5,342,876 A | 8/1994 | Abe et al. |
| 5,350,624 A | 9/1994 | Georger et al. |
| 5,366,947 A | 11/1994 | Müller et al. |
| 5,382,400 A | 1/1995 | Pike et al. |
| 5,383,450 A | 1/1995 | Hubbard et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,427,844 A | 6/1995 | Murai et al. |
| 5,429,628 A | 7/1995 | Trinh et al. |
| 5,432,000 A | 7/1995 | Young, Sr. et al. |
| 5,451,450 A | 9/1995 | Erderly et al. |
| 5,458,864 A | 10/1995 | Tsugeno et al. |
| 5,472,775 A | 12/1995 | Obijeski et al. |
| 5,480,636 A | 1/1996 | Maruo et al. |
| 5,486,356 A | 1/1996 | Yim |
| 5,487,938 A | 1/1996 | Spencer et al. |
| 5,488,126 A | 1/1996 | Subramanian et al. |
| 5,527,171 A | 6/1996 | Soerensen |
| 5,538,548 A | 7/1996 | Yamazaki |
| 5,539,124 A | 7/1996 | Etherton et al. |
| 5,540,916 A | 7/1996 | Parks |
| 5,547,607 A | 8/1996 | Ando et al. |
| 5,553,608 A | 9/1996 | Reese et al. |
| 5,554,775 A | 9/1996 | Krishnamurti et al. |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,616,315 A | 4/1997 | Masterman et al. |
| 5,661,198 A | 8/1997 | Inatani et al. |
| 5,663,224 A | 9/1997 | Emmons et al. |
| 5,679,138 A | 10/1997 | Bishop et al. |
| 5,679,724 A | 10/1997 | Sacripante et al. |
| 5,695,868 A | 12/1997 | McCormack |
| 5,705,216 A * | 1/1998 | Tyson ........................ 426/478 |
| 5,733,272 A | 3/1998 | Brunner et al. |
| 5,773,227 A | 6/1998 | Kuhn et al. |
| 5,795,985 A | 8/1998 | Hüsler et al. |
| 5,813,398 A | 9/1998 | Baird et al. |
| 5,817,300 A | 10/1998 | Cook et al. |
| 5,837,352 A | 11/1998 | English et al. |
| 5,843,509 A | 12/1998 | Calvo Salve et al. |
| 5,855,788 A | 1/1999 | Everhart et al. |
| 5,858,503 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |
| 5,882,638 A | 3/1999 | Dodd et al. |
| 5,885,599 A | 3/1999 | Peterson et al. |
| 5,897,541 A | 4/1999 | Uitenbroek et al. |
| 5,902,226 A | 5/1999 | Tasaki et al. |
| 5,905,101 A | 5/1999 | Fujiki et al. |
| 5,916,596 A | 6/1999 | Desai et al. |
| 5,948,398 A | 9/1999 | Hanamoto et al. |
| 5,948,483 A | 9/1999 | Kim et al. |
| 5,962,566 A | 10/1999 | Grandfils et al. |
| 5,964,926 A | 10/1999 | Cohen |
| 5,972,389 A | 10/1999 | Shell et al. |
| 5,985,229 A | 11/1999 | Yamada et al. |
| 5,989,510 A | 11/1999 | Abe et al. |
| 5,989,515 A | 11/1999 | Watanabe et al. |
| 5,998,222 A | 12/1999 | Weimer |
| 6,004,625 A | 12/1999 | Ohshima |
| 6,007,592 A | 12/1999 | Kasai et al. |
| 6,024,786 A | 2/2000 | Gore |
| 6,045,900 A | 4/2000 | Haffner et al. |
| 6,047,413 A | 4/2000 | Welchel et al. |
| 6,060,410 A | 5/2000 | Gillberg-LaForce et al. |
| 6,073,771 A | 6/2000 | Pressley et al. |
| 6,075,179 A | 6/2000 | McCormack et al. |
| 6,096,299 A | 8/2000 | Guarracino et al. |
| 6,111,163 A | 8/2000 | McCormack et al. |
| 6,172,173 B1 | 1/2001 | Spencer et al. |
| 6,177,608 B1 | 1/2001 | Weinstrauch |
| 6,190,814 B1 | 2/2001 | Law et al. |
| 6,193,844 B1 | 2/2001 | McLaughlin et al. |
| 6,200,555 B1 | 3/2001 | Nishijima et al. |

| | | |
|---|---|---|
| 6,210,625 B1 | 4/2001 | Matsushita et al. |
| 6,225,524 B1 | 5/2001 | Guarracino et al. |
| 6,238,767 B1 | 5/2001 | McCormack et al. |
| 6,254,894 B1 | 7/2001 | Denkewicz, Jr. et al. |
| 6,264,615 B1 | 7/2001 | Diamond et al. |
| 6,277,346 B1 | 8/2001 | Murasawa et al. |
| 6,277,489 B1 | 8/2001 | Abbott et al. |
| 6,277,772 B1 | 8/2001 | Gancet et al. |
| 6,291,535 B1 | 9/2001 | Watanabe et al. |
| 6,294,222 B1 | 9/2001 | Cohen et al. |
| 6,299,867 B1 | 10/2001 | Aoyagi et al. |
| 6,309,736 B1 | 10/2001 | McCormack et al. |
| 6,315,864 B2 | 11/2001 | Anderson et al. |
| 6,334,988 B1 | 1/2002 | Gallis et al. |
| 6,344,218 B1 | 2/2002 | Dodd et al. |
| 6,344,272 B1 | 2/2002 | Oldenburg et al. |
| 6,358,537 B1 | 3/2002 | Hoshino et al. |
| 6,358,909 B1 | 3/2002 | Ochomogo et al. |
| 6,361,780 B1 | 3/2002 | Ley et al. |
| 6,369,290 B1 | 4/2002 | Glaug et al. |
| 6,376,741 B1 | 4/2002 | Guarracino et al. |
| 6,387,495 B1 | 5/2002 | Reeves et al. |
| 6,398,827 B1 | 6/2002 | Ota et al. |
| 6,410,616 B1 | 6/2002 | Harada et al. |
| 6,410,765 B1 | 6/2002 | Wellinghoff et al. |
| 6,425,530 B1 | 7/2002 | Coakley |
| 6,427,693 B1 | 8/2002 | Blackstock et al. |
| 6,428,814 B1 | 8/2002 | Bosch et al. |
| 6,432,872 B1 | 8/2002 | Tsushio et al. |
| 6,433,243 B1 | 8/2002 | Woltman et al. |
| 6,440,187 B1 | 8/2002 | Kasai et al. |
| 6,460,989 B1 | 10/2002 | Yano et al. |
| 6,461,735 B1 | 10/2002 | Furuya et al. |
| 6,467,897 B1 | 10/2002 | Wu et al. |
| 6,468,500 B1 | 10/2002 | Sakaguchi et al. |
| 6,475,601 B1 | 11/2002 | Sakaki et al. |
| 6,479,150 B1 | 11/2002 | Liu et al. |
| 6,491,790 B1 | 12/2002 | Proverb et al. |
| 6,498,000 B2 | 12/2002 | Murasawa et al. |
| 6,517,199 B1 | 2/2003 | Tomioka et al. |
| 6,531,704 B2 | 3/2003 | Yadav et al. |
| 6,536,890 B1 | 3/2003 | Kato et al. |
| 6,548,264 B1 | 4/2003 | Tan et al. |
| 6,551,457 B2 | 4/2003 | Westman et al. |
| 6,562,441 B1 | 5/2003 | Maeda et al. |
| 6,575,383 B2 | 6/2003 | Dobler et al. |
| 6,578,521 B2 | 6/2003 | Raymond et al. |
| 6,589,562 B1 | 7/2003 | Shefer et al. |
| 6,607,711 B2 | 8/2003 | Pedersen |
| 6,623,848 B2 | 9/2003 | Brehm et al. |
| 6,638,918 B2 | 10/2003 | Davison et al. |
| 6,639,004 B2 | 10/2003 | Falat et al. |
| 6,645,569 B2 | 11/2003 | Cramer et al. |
| 6,680,279 B2 | 1/2004 | Cai et al. |
| 6,693,071 B2 | 2/2004 | Ghosh et al. |
| 7,008,979 B2 | 3/2006 | Schottman et al. |
| 7,141,518 B2 * | 11/2006 | MacDonald et al. .......... 442/59 |
| 2001/0000889 A1 | 5/2001 | Yadav et al. |
| 2001/0023338 A1 | 9/2001 | Guarracino et al. |
| 2001/0031248 A1 | 10/2001 | Hall-Puzio et al. |
| 2001/0051189 A1 * | 12/2001 | Fernandez et al. .......... 424/499 |
| 2001/0056246 A1 | 12/2001 | Rodriguez-Fernandez et al. |
| 2002/0004350 A1 * | 1/2002 | Morman et al. .......... 442/381 |
| 2002/0005145 A1 | 1/2002 | Sherman |
| 2002/0022672 A1 * | 2/2002 | Thunhorst et al. .......... 521/50.5 |
| 2002/0066542 A1 | 6/2002 | Jakob et al. |
| 2002/0091071 A1 | 7/2002 | Fischer et al. |
| 2002/0106466 A1 | 8/2002 | Hausmann et al. |
| 2002/0110686 A1 | 8/2002 | Dugan |
| 2002/0128336 A1 | 9/2002 | Kolb et al. |
| 2002/0142937 A1 | 10/2002 | Carter et al. |
| 2002/0149656 A1 | 10/2002 | Nohr et al. |
| 2002/0150678 A1 | 10/2002 | Cramer et al. |
| 2002/0151634 A1 * | 10/2002 | Rohrbaugh et al. .......... 524/430 |
| 2002/0176982 A1 | 11/2002 | Rohrbaugh et al. |
| 2002/0177621 A1 | 11/2002 | Hanada |
| 2002/0182102 A1 | 12/2002 | Fontenot et al. |
| 2003/0013369 A1 | 1/2003 | Soane et al. |
| 2003/0021983 A1 | 1/2003 | Nohr et al. |
| 2003/0050211 A1 | 3/2003 | Hage et al. |
| 2003/0056648 A1 | 3/2003 | Fornai et al. |
| 2003/0070782 A1 | 4/2003 | Proverb et al. |
| 2003/0082237 A1 | 5/2003 | Cha et al. |
| 2003/0099718 A1 | 5/2003 | Burrell et al. |
| 2003/0100842 A1 | 5/2003 | Rosenberg et al. |
| 2003/0147956 A1 | 8/2003 | Shefer et al. |
| 2003/0147966 A1 | 8/2003 | Franzen et al. |
| 2003/0181540 A1 | 9/2003 | Quellet et al. |
| 2003/0203009 A1 * | 10/2003 | MacDonald .......... 424/443 |
| 2003/0235605 A1 | 12/2003 | Lelah et al. |
| 2004/0033269 A1 | 2/2004 | Hei et al. |
| 2004/0034157 A1 | 2/2004 | Ghosh et al. |
| 2004/0043688 A1 | 3/2004 | Soerens et al. |
| 2004/0122387 A1 | 6/2004 | Long et al. |
| 2005/0084412 A1 * | 4/2005 | MacDonald et al. .......... 422/5 |
| 2005/0084438 A1 * | 4/2005 | Do et al. .......... 423/244.02 |
| 2005/0084464 A1 * | 4/2005 | McGrath et al. .......... 424/67 |

FOREIGN PATENT DOCUMENTS

| | | |
|---|---|---|
| EP | 0282287 | 4/1996 |
| EP | 0972563 | 1/2000 |
| EP | 0749295 | 7/2000 |
| EP | 1034800 A1 | 9/2000 |
| EP | 1053788 | 11/2000 |
| EP | 1157672 | 11/2001 |
| EP | 1157672 A1 | 11/2001 |
| EP | 1162172 A1 | 12/2001 |
| EP | 1188854 A1 | 3/2002 |
| EP | 1214878 A1 | 6/2002 |
| EP | 1216675 A1 | 6/2002 |
| EP | 1298071 | 4/2003 |
| EP | 1315526 B1 | 6/2003 |
| JP | 62149322 | 7/1987 |
| JP | 3221142 | 9/1991 |
| WO | WO8902698 A1 | 4/1989 |
| WO | WO9111977 A1 | 8/1991 |
| WO | WO9112029 A1 | 8/1991 |
| WO | WO9112030 A1 | 8/1991 |
| WO | WO9619346 A2 | 6/1996 |
| WO | WO9619346 A3 | 6/1996 |
| WO | WO9725076 A1 | 7/1997 |
| WO | WO 98/20915 | 5/1998 |
| WO | WO9820915 A1 | 5/1998 |
| WO | WO 98/26808 | 6/1998 |
| WO | WO9826808 A2 | 6/1998 |
| WO | WO9826808 A3 | 6/1998 |
| WO | WO 99/47252 | 9/1999 |
| WO | WO 00/03797 | 1/2000 |
| WO | WO0013764 A1 | 3/2000 |
| WO | WO0029036 A2 | 3/2000 |
| WO | WO0029036 A3 | 3/2000 |
| WO | WO0059555 A1 | 10/2000 |
| WO | WO 00/76558 | 12/2000 |
| WO | WO0076558 A1 | 12/2000 |
| WO | WO 01/06054 | 1/2001 |
| WO | WO 02/26272 | 4/2002 |
| WO | WO 02/49559 | 6/2002 |
| WO | WO 02/55115 | 7/2002 |
| WO | WO 02/62881 | 8/2002 |
| WO | WO 02/64877 | 8/2002 |
| WO | WO 02/83297 | 10/2002 |
| WO | WO 02/84017 | 10/2002 |
| WO | WO 02/95112 | 11/2002 |
| WO | WO02094329 A1 | 11/2002 |
| WO | WO 03/00979 | 1/2003 |

| | | |
|---|---|---|
| WO | WO 03/025067 | 3/2003 |
| WO | WO 03/25067 | 3/2003 |
| WO | WO03032959 A1 | 4/2003 |
| WO | WO03088931 A2 | 10/2003 |
| WO | WO 03/092885 | 11/2003 |
| WO | WO2004000986 A1 | 12/2003 |
| WO | WO2006000378 A2 | 7/2004 |

OTHER PUBLICATIONS

Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5261246, Oct. 12, 1993.
Abstract of Japanese Patent No. JP6285140, Oct. 11, 1994.
Abstract of Japanese Patent No. JP63072337, Apr. 2, 1988.
Abstract of Japanese Patent No. JP8152409, Jun. 11, 1996.
Abstract of SU834073, May 30, 1981.
PCT Search Report and Written Opinion for PCT/US2004/011596, Aug. 30, 2004.
PCT Search Report and Written Opinion for PCT/US2004/016933, Nov. 2, 2004.
Article—*Immunization of mice with peptomers covalently couopled to aluminum oxide nanoparticles*, Andreas Frey, Nicholas Mantis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.
PCT Search Report for PCT/US03/39737, Jun. 18, 2004.
Abstract of Japanese Patent No. 7256025, Oct. 9, 1995.
PCT Search Report for PCT/US03/32846, Jun. 7, 2004.
Derwent Abstract, JP 5106199A, Apr. 1993, Nakajima et al.
Derwent Abstract, JP 9143872A, Jun. 1997, Sogawa.
Brunauer, S. et al., "Adsorption of Gases in Multimolecular Layers", *Journal of American Chemical Society*, vol. 60, Feb. 1938, pp. 309-319.
Béné, A. et al., "Applicability of a SPME Method for the Rapid Determination of VOCs", *Chimia*, 56, No. 6, 2002, ISSN 0009-4293, pp. 289-291.
Malik, D.J. et al., "Characterisation of Novel Modified Active Carbons and Marine Algal Biomass for the Selective Adsorption of Lead", *Water Research*, 36, 2002, pp. 1527-1538.
Cost, F., *Pocket Guide to Digital Printing*, Delmar Publishers, Albany, NY, ISBN 0-8273-7592-1, pp. 144-145, 1997.
Noller, C.R., "Saponins and Sapogenins. VIII. Surface Films of Echinocystic Acid and Derivatives", *The Journal of the American Chemical Society*, vol. 60, 1938, 3 pages.
Antonietti, M., "Synthesis of porous Silica with help from cyclodextrin aggregates", Max-Planck-Institut für Kolloid-und, Germany, 1 page, Dec. 5, 2001.
Maldotti, A. et al., "Immobilization of $(n-Bu_4N)_4W_{10}O_{32}$ on Mesoporous MCM-41 and Amorphous Silicas for Photocatalytic Oxidation of Cycloalkanes with Molecular Oxygen", *Journal of Catalysis*, vol. 209, 2002, pp. 210-216.
Zhang, Q. et al., "Fe-MCM-41 for Selective Epoxidation of Styrene with Hydrogen Peroxide", *The Chemical Society of Japan*, Chemistry Letters 2001, pp. 946-947.
Melde, B.J. et al., "Mesoporous Sieves with Unified Hybrid Inorganic/Organic Frameworks", *Chem. Mater.*, vol. 11, No. 11, 1999, pp. 3302-3308.
Polarz, S. et al., "From Cyclodextrin Assemblies to Porous Materials by Silica Templating", *Angew. Chem. Int. Ed.*, vol. 40, No. 23, 2001, pp. 4417-4421.
Shi, D. et al., "Uniform Deposition of Ultrathin Polymer Films on the Surfaces of $Al_2O_3$ Nanoparticles by a Plasma Treatment", University of Cincinnati and University of Michigan, Jun. 2000, pp. 1-15.
Santra, S. et al., "Development of novel dye-doped silica nanoparticles for biomarker application", *Journal of Biomedical Optics*, vol. 6, No. 2, Apr. 2001, pp. 160-166.
Buchhammer, M. et al., "Nanoparticles based on polyelectrolyte complexes: effect of structure and net charge on the sorption capacility for solved organic molecules", *Colloid Polym. Sci.*, vol. 278, 2000, pp. 841-847.
Brunauer, S. et al., "Adsorption of Gases in Multimolecular Layers", *The Journal of the American Chemical Society*, vol. 60, Feb. 1938, pp. 309-319.
Schaber, P.M. et al., "Study of the urea thermal decomposition (pyrolsis) reaction and importance to cyanuric acid production", *American Laboratory*, Aug. 1999, pp. 13-21.
Bergna, H.E., Editor, "Silanol Groups, Siloxane Bridges, and Physically Adsorbed Water", The Colloid Chemistry of Silica, American Chemical Society $200^{th}$ National Meeting, Aug. 26-31, 1990, pp. 22-23 and pp. 52-59.
Schweigert, I.V. et al., "Structure and properties of silica nanoclusters at high temperatures", *The American Physical Society*, Physical Review B, vol. 65, No. 235410, pp. 1-9, 2002.
Biermann, C.J. et al., Grafting of Poly(ethylenimine) onto Mesylated Cellulose Acetate, Poly(methyl methacrylate) and Poly(vinyl chloride), *Carbohydrate Polymers*, vol. 12, 1990, pp. 323-327.
Yurieva, T.M. et al., Abstract of "Non-hydrothermal synthesis of copper-, zinc- and copper-zinc hydrosilicates", *Materials Research Innovations*, vol. 5, No. 1, Jun. 2001, 2 pages.
Article—*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222-228.
Article—*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.
Product Information Sheet for Snowtex®, 6 pages, Mar. 5, 2001.
Article—*Significance of Ammonia in the Genesis of Gastric Epithelial Lesions Induced by Helicobacter pylori: An in vitro Study with Different Bacterial Strains and Urea Concentrations*, P. Sommi, V. Ricci, R. Fiocca, M. Romano, K.J. Ivey, E. Cova, E. Solcia, and U. Ventura, Digestion, vol. 57, 1996, pp. 299-304.
Article—*Ammonia vapour in the mouth as a diagnostic marker for Helicobacter pylori infection: preliminary "proof of principle" pharmacological investigations*, C. D. R. Dunn, M. Black, D. C. Cowell, C. Penault, N. M. Ratcliffe, R. Spence, and C. Teare, British Journal of Biomedical Science, vol. 58, 2001, pp. 66-76.
Article—*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.
Article—*Validation of $^{13}C$-Urea Breath Test for the Diagnosis of Helicobacter Pylori Infection in the Singapore Population*, T. S. Chua, K. M. Fock, E. K. Teo, T. M. Ng, Singapore Medical Journal, vol. 43, No. 8, 2002, pp. 408-411.
Article—*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.
Article—*Spectrophotometric Assay of Thiols*, Peter C. Jocelyn, Methods in Enzymology, vol. 142, 1987, pp. 44-67.

* cited by examiner

ODOR ABSORBING EXTRUDATES

BACKGROUND OF THE INVENTION

This invention concerns odor absorbing extrudates like fibers and films and methods of making them.

Methods of minimizing the effect of odorous compounds include, for example, covering up the odor by releasing an even stronger odor. Air freshener sprays and candles are examples of this method. Another way to combat odorous compounds, including ammonia, methyl mercaptan, trimethylamine, and other sulfides and amines is to remove these compounds through the use of deodorizing agents that will absorb them. Activated charcoal and sodium bicarbonate are two compounds commonly used to absorb odors. Activated charcoal, however, typically has a low deodorizing ability, especially for ammonia odors and when in the presence of moisture, and the black color of charcoal lacks aesthetically pleasing characteristics generally desired by consumers. Sodium bicarbonate, and other white colored odor absorbents such as silica gel and zeolites generally have a lower absorbency than activated charcoal and so are less effective.

In addition to removing foul smelling compounds, there is a need for products capable of removing gases that, while not necessarily odorous, still cause a negative effect. One example of such a gaseous compound is ethylene, which is released by fruit as it ripens. Removal of the ethylene gas would slow and potentially control the ripening process, allowing for extended storage and transportation.

There is thus a need for a gas and/or odor removal/neutralizing extrudate.

SUMMARY OF THE INVENTION

In response to the difficulties and problems encountered in the prior art, a new extrudate has been developed which has modified high surface area particles that absorb odors and gasses. The extrudates have high surface area materials and at least one metal ion adsorbed onto the high surface area material. The extrudates may be breathable films, multilayer laminates and pultruded articles.

The extrudates may be made into storage and packaging material to reduce odor and retard the ripening of fruit. The extrudates, if in the form of a breathable film or multilayer laminate may be used as outer cover material for personal care products like diapers, adult incontinence products, training pants and the like.

The extrudates of the invention are made using fillers that have been treated with modified high surface area particles. The high surface area particles have been modified by the addition of metal ions which absorb odors and gasses.

DETAILED DESCRIPTION

The invention concerns extrudates which have odor absorbing, high surface area materials, such as nanoparticles, modified with at least one metal ion. The modified high surface area materials of this invention are useful in removing gaseous compounds and/or odorous compounds. While the invention will be described hereinafter with particular reference to nanoparticles, it will be understood that the invention is useful with various nanoparticles. "Gaseous compound" or "gas" includes any molecule or compound that can exist as a gas or vapor. "Odorous compound" or "odor" refers to any molecule or compound detectable to the olfactory system.

Extrudates include films and any other form which may result from material being pushed, usually by pressure, through a die. Extrudates may be flexible or rigid depending upon the thickness and the materials from which they are made. The term "extrudates" is also intended to encompass materials made through processes known as "pultrusion" wherein a base material (e.g. glass fiber roving) and a resin is pulled through a die, usually with heating, rather than being pushed through a die.

The term "film" for the purpose of this invention means a breathable film such as, for example, microporous films having a WVTR of at least 300 g/m$^2$/day, and more desirably having a WVTR in excess about 500 g/m$^2$/day, 800 g/m$^2$/day, 1500 g/m$^2$/day or even exceeding 3000 g/m$^2$/day.

The water vapor transmission rate (WVTR) test used herein was ASTM Standard E96-80. Circular samples measuring three inches (7.6 cm) in diameter were cut from each of the test materials and a control which was a piece of CELGARD™ 2500 microporous polypropylene film from Hoechst Celanese Corporation of Somerville, N.J., USA. One hundred milliliters of water were poured into a test dish and individual samples of the test materials and control material were placed across the open tops of the individual dishes. The test dish was a number 60-1 Vapometer dish distributed by Thwing-Albert Instrument Company of Philadelphia, Pa., USA. Screw-on flanges were tightened to form a seal along the edges of the dish, leaving the associated test material or control material exposed to the ambient atmosphere over a 6.5 centimeter diameter circle having an exposed area of approximately 33.17 square centimeters. The dishes were placed in a forced air oven at 37° C. for 1 hour to equilibrate. The oven was a constant temperature oven with external air circulating through it to prevent water vapor accumulation inside. A suitable forced air oven is, for example, a Blue-M Power-O-Matic 60 oven distributed by Blue M. Electric Company of Blue Island, Ill., USA. Upon completion of the equilibration, the dishes were removed from the oven, weighed an immediately returned to the oven. After 24 hours, the dishes were removed from the oven and weighed again. The preliminary test water vapor transmission rate values were calculated with Equation (I) below:

$$\text{Test WVTR} = (\text{grams weight loss over 24 hours}) \times 315.5 \text{ g/m}^2/24 \text{ hours} \quad (I)$$

The relative humidity within the oven was not specifically controlled.

Under the predetermined set conditions of 37° C. and ambient relative humidity, the WVTR for the CELGARD™ 2500 control material was found to be 5000 grams per square meter for 24 hours. Accordingly, the control sample was run with each test and the preliminary test values were corrected to set conditions using Equation (II) below:

$$\text{WVTR} = (\text{Test WVTR/control WVTR}) \times (5000 \text{ g/m}^2/24 \text{ hours}) \quad (II)$$

Figure 1:
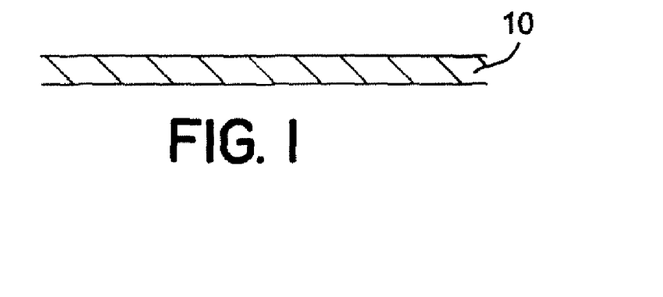
FIG. 1 is a cross-sectional view of a film.

The extrudate of the present invention may be a breathable barrier film or laminate comprising, in reference to FIG. 1, a film 10 which may be a multilayer film.

The breathable film is desirably a stretched-filled film which includes a thermoplastic polymer and filler. The components can be mixed together, heated and then extruded into a monolayer or multilayer film. The film is usually then stretched in at least one direction to reduce the film gauge or thickness and to create a network of micropores of a size and frequency needed to achieve the desired level of breathability.

Figure 2:
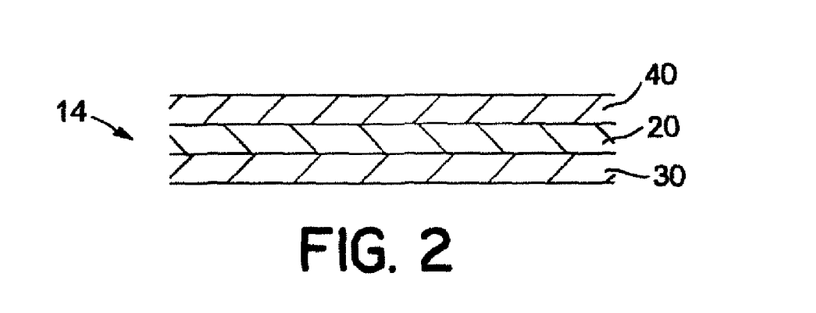
FIG. 2 is a cross-sectional view of a multilayer film.

The filled film may be made by any one of a variety of film forming processes known in the art such as, for example, by using either cast or blown film equipment. In the case of a multilayer film as shown in FIG. 2, the layers 20, 30, 40 are desirably simultaneously made such as, for example, forming by co-extrusion as disclosed in U.S. Pat. Nos. 4,522,203, 4,494,629 and 4,734,324. Examples of breathable barrier films suitable for use with the present invention are described in U.S. Pat. Nos. 5,695,868, 6,309,736, 6,075,179, and 6,111, 163. Such films, prior to stretching, desirably have a basis weight of less than about 100 g/m$^2$ and even more desirably less than about 60 g/m$^2$. Upon stretching, multilayer films desirably have a basis weight of less than 60 g/m$^2$ and even more desirably between about 15 and 35 g/m$^2$.

Stretching may be performed by a machine direction orienter, a commercially available device from the Marshall and Williams Company of Providence, R.I., USA. A machine direction orienter has a plurality of preheat and stretching rollers which stretch and thin an unstretched multilayer film in the machine direction. The film can be stretched in either a single or multiple stretching operations and may be stretched in multiple directions. After stretching the film may be allowed to slightly retract and/or be further heated or annealed by one or more heated rollers.

Thermoplastic polymers used in the fabrication of extrudates of the present invention include polyolefins including homopolymers, copolymers, terpolymers and blends thereof. Flexible polyolefins, ethylene elastomers or "polyolefin based" films are also believed suitable for use in the present invention. A polymer is considered to be "polyolefin-based" if the polymeric portion of the film, exclusive of any filler materials, has at least 50 weight percent polyolefin.

Ethylene elastomers comprise polymers wherein the ethylene monomers are polymerized with an alpha-olefin such that the resulting polymer composition has a narrow molecular weight distribution (Mw/Mn) of about 2, homogeneous branching and controlled long chain branching. Suitable alpha-olefins include 1-octene, 1-butene, 1-hexene and 4-methyl-pentene. Exemplary polymers include those made by "metallocene", "constrained geometry" or "single-site" catalysts such as those described in U.S. Pat. No. 5,472,775 to Obijeski et al.; U.S. Pat. No. 5,451,450 to Erderly et al.; U.S. Pat. No. 5,204,429 to Kaminsky et al.; U.S. Pat. No. 5,539, 124 to Etherton et al.; and U.S. Pat. No. 5,554,775 to Krishnamurti et al. The metallocene process generally uses a metallocene catalyst which is activated, i.e. ionized, by a co-catalyst. Suitable low density ethylene elastomers are commercially available from Dow Chemical Company of Midland, Mich., USA under the tradename AFFINITY® and from Exxon Chemical Co. of Houston, Tex., USA, under the trade name EXACT®.

Additional commercially available polyolefin polymer components include Catalloy polymers which are olefinic multistep reactor products wherein an amorphous ethylene propylene random copolymer is molecularly dispersed in a predominantly semi crystalline high propylene monomer/low ethylene monomer continuous matrix, an example of which is described in U.S. Pat. No. 5,300,365 to Ogale. Catalloy polymers are available from Montell Polyolefins, a division of Basell USA, Wilmington, Del., USA.

Additional film forming polymers which may be suitable for use with the present invention, alone or in combination with other polymers, include ethylene vinyl acetate (EVA), ethylene ethyl acrylate (EEA), ethylene acrylic acid (EAA), ethylene methyl acrylate (EMA), ethylene normal butyl acrylate (EnBA), polyester, polyethylene terephthalate (PET), nylon, ethylene vinyl alcohol (EVOH), polystyrene (PS), polyurethane (PU), polybutylene (PB), and polybutylene terephthalate (PBT). Polyolefin polymers, however, are preferred and these include polymers of ethylene and propylene as well as copolymers, terpolymers and blends thereof. Examples of such polyolefin polymers include linear low density polyethylene (LLDPE) and ethylene-propylene copolymer blends.

A film may also optionally include one or more stabilizers such as, for example, a hindered phenol stabilizer. Commercially available anti-oxidants include IRGANOX® E 17 (alpha-tocopherol) and IRGANOX® 1076 (octodecyl 3,5-ditert-butyl-4-hydroxyhy-drocinnamate) which are available from Ciba Specialty Chemicals of Tarrytown, N.Y. USA. About 100 to 1000 ppm of the stabilizer may be added to the base polymer(s) prior to extrusion. (Parts per million is in reference to the entire weight of the filled film.) Other stabilizers or additives which are compatible with the film forming process, stretching and any subsequent lamination steps may also be employed with the present invention. Additional additives may be added to impart desired characteristics to the film such as, for example, melt stabilizers, processing stabilizers, heat stabilizers, light stabilizers, heat aging stabilizers and other additives known to those skilled in the art. Examples include DOVER-PHOS® melt stabilizer available from Dover Chemical Corp. of Dover, Ohio, USA, and CHIMASSORB® 944 and 119 hindered amine stabilizers and IRGAFOS® 168 phosphite stabilizer available from Ciba Specialty Chemicals.

A film may further include various extenders, waxes and other additives as is known to those skilled in the art.

In addition to the thermoplastic polymers, the extrudates of this invention include a filler which is used to incorporate modified nanoparticles into the extrudate. Breathable stretched-filled films also include a filler to impart breathability to the film upon stretching.

As used herein, "filler" is meant to include particulates and/or other forms of materials which can be added to the polymer extrusion blend which will not chemically interfere with or adversely affect the extrudate and further which can be dispersed throughout the extrudate. The fillers will generally be in particulate form with average particle sizes in the range of about 0.1 to about 10 microns, desirably from about 0.1 to about 4 microns. As used herein the term "particle size" describes the largest dimension or length of the filler. Both organic and inorganic fillers are contemplated for use with the present invention provided they do not interfere with the extrusion process and/or subsequent laminating processes.

Examples of fillers include calcium carbonate ($CaCO_3$), various clays, silica ($SiO_2$), alumina, barium sulfate, talc, magnesium sulfate, titanium dioxide, zeolites, aluminum sulfate, cellulose-type powders, diatomaceous earth, gypsum, magnesium sulfate, magnesium carbonate, barium carbonate, kaolin, mica, carbon, magnesium oxide, aluminum hydroxide, pulp powder, wood powder, cellulose derivatives, polymeric particles, chitin and chitin derivatives.

The filler particles may optionally be coated with a fatty acid, such as stearic acid or behenic acid, and/or other material in order to facilitate the free flow of the particles (in bulk) and their ease of dispersion into the polymer. A filled film, for example, will usually contain at least about 35% filler based upon the total weight of the base film layer, more desirably from about 45% to about 65% by weight filler.

FIG. 2 shows a multilayer film 14 having a base layer 20 and two outer layers 30, 40. This film 14, prior to stretching, desirably has a basis weight of less than about 100 grams per square meter (gsm) and even more desirably less than about 60 gsm. Upon stretching the multilayer film 14 desirably has a basis weight of less than 60 gsm and even more desirably between about 15 and 35 gsm. Typically such lower basis weight films have a thickness of about 15 microns to about 30 microns. The base film 20 desirably comprises from about 50% to about 98% of the multilayer film thickness and the outer layers 30, 40 desirably comprise from about 2% up to about 50%, more desirably from about 5% up to about 20%, of the total thickness of the multilayer film.

Figure 3:
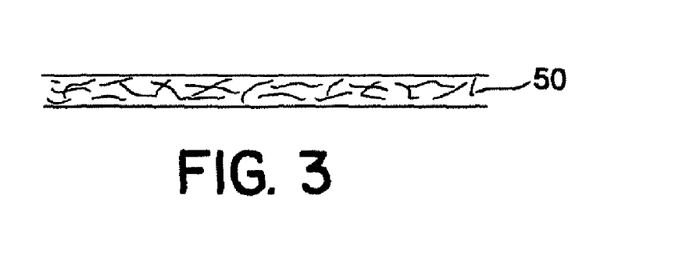
FIG. 3 is a cross-sectional view of a nonwoven fabric.
Figure 4:
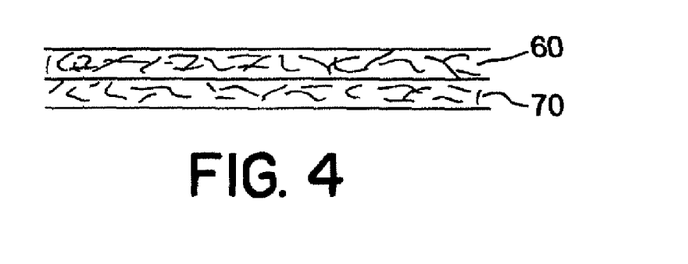
FIG. 4 is a cross-sectional view of a nonwoven fabric laminate.

In another aspect the present invention may be a laminate of breathable films and nonwoven fabrics provided the film contains odor absorbing, nanoparticles. A nonwoven fabric comprises, in reference to FIG. 3, fibers 50. The nonwoven fabric may be a multilayer nonwoven laminate as shown in FIG. 4 having layers 60, 70 made from fabrics produced by different processes. Multilayer laminates generally may have a number of nonwoven layers in many different configurations and may include other materials like films.

The nonwoven fabric may be made according to processes like spunbonding, meltblowing, airlaying, bonding and carding, and so forth. Nonwoven fabrics may be made from thermoplastic resins including any of those mentioned above for film production.

The term "fibers" means small diameter fibers having an average diameter not greater than about 75 microns, for example, having an average diameter of from about 0.5 microns to about 50 microns, or more particularly, fibers may have an average diameter of from about 2 microns to about 40 microns.

A nonwoven fabric is a structure of individual fibers or threads which are interlaid, but not in an identifiable manner as in a knitted fabric. Nonwoven fabrics or webs have been formed from many processes such as for example, meltblowing processes, spunbonding processes, airlaying and bonded carded web processes as described in more detail below. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbonded fibers" are small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

A bonded carded web is made from staple fibers which are sent through a combing or carding unit, which breaks apart and aligns the staple fibers in the machine direction to form a generally machine direction-oriented fibrous nonwoven web. Once the web is formed, it then is bonded by one or more of several methods such as powder bonding, pattern bonding, through air bonding and ultrasonic bonding.

In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another. Examples of airlaid teachings include the DanWeb process as described in U.S. Pat. No. 4,640,810 to Laursen et al. and assigned to Scan Web of North America Inc, the Kroyer process as described in U.S. Pat. No. 4,494,278 to Kroyer et al. and U.S. Pat. No. 5,527,171 to Soerensen assigned to Niro Separation a/s, the method of U.S. Pat. No. 4,375,448 to Appel et al assigned to Kimberly-Clark Corporation, or other similar methods.

In still another aspect of the invention, filler having the modified nanoparticles may be used in the pultrusion process. Pultrusion is a manufacturing process for producing continuous lengths of structural shapes. Raw materials include a liquid resin mixture (containing resin, fillers and specialized additives) and reinforcing fibers. The process involves pulling these raw materials (rather than pushing as in the case of extrusion) through a heated steel forming die using a continuous pulling device. Pultruded shapes may be used for odor and gas control in the form of countertops, railings, tubes, rods and other structural materials and the like in pulp and paper mills, chemical plants, oil refineries, hotels and motels, ships, planes and submarines and so forth.

The nanoparticles used in the practice of this invention act as carriers for at least one metal ion present on the surface of the nanoparticle, and the metal ion creates an active site that binds with at least one gaseous compound and/or odorous compound thereby removing the compound from the surrounding environment. Nanoparticles can also absorb certain gaseous compounds and/or odorous compounds from the surrounding environment by adsorption directly onto the surface area of the nanoparticles. Silica nanoparticles modified by copper ions or alternatively, by silver ions, for example, were demonstrated to be effective in removing amine and sulfur based classes of odorous compounds.

Gas and/or odor removing particles of this invention are modified nanoparticles. Nanoparticles useful in this invention have a large surface area due to the small size of the individual particles of the high surface area material. Nanoparticles useful in this invention have a suitable surface area of at least about 50 square meters/gram, suitably at least about 100 square meters/gram, and more suitably at least about 200 square meters/gram, and still more suitably at least about 500 square meters/gram or more.

"Nanoparticle" refers to a high surface material having a particle diameter of less than about 500 nanometers. Nanoparticles useful in this invention include silica, alumina, magnesium oxide, titanium dioxide, iron oxide, gold, zinc oxide, copper oxide, organic nanoparticles such as polystyrene, and combinations thereof. Nanoparticles are not generally ionic yet still have an overall electric Zeta Potential. "Zeta Potential" refers to the electrical potential, or electrokinetic potential, that exists across the interface of all solids and liquids. Naturally occurring chemical reactions on the surface of a nanoparticle result in the Zeta Potential of that nanoparticle and nanoparticles may have either positive or negative Zeta Potentials. Silica nanoparticles, for example, are tetrahedral complexes of silicon dioxide molecules. On the surface of the silica particles the silicon dioxide molecules can undergo chemical reactions forming silanol groups (SiOH) which react with other silanol groups to form siloxane bonds (Si—O—Si bonds). The dehydration reactions of the silanol groups to form the silanol bond and the reverse reactions result in a negative Zeta Potential and allow positively charged metal ions to adsorb onto the silica.

The nanoparticles useful in this invention will typically have a first Zeta Potential and a second Zeta Potential after adsorption of the metal ion onto the nanoparticle due to the addition of the oppositely-charged metal ions. The Zeta Potential change of the nanoparticle is related to the quantity of metal ions adsorbed onto the nanoparticle. This relationship provides a measurement for determining the amount of adsorbed metal ions and a method for controlling the amount of adsorption. For instance, the addition of a dilute solution of copper chloride drop-wise to a silica nanoparticle solution until the Zeta Potential of the silica suspension changed from −25 millivolts to a higher Zeta Potential, such as in the range of about −5 millivolts to −15 millivolts, was found to provide a sufficient concentration of metal ions adsorbed onto the nanoparticles to remove particular odorous compounds. The nanoparticle may have a difference between the first and second Zeta Potential of at least about 1.0 millivolt and suitably at least about 5.0 millivolts.

The nanoparticles are modified with metal ions that bond with compounds such as gases and odorous compounds. "Metal ion" refers to salt ions and/or ion complexes of transition metal elements designated as IB through VIIIB on the periodic table. Other ions can be used in the invention as well. Metal ions are adsorbed onto nanoparticles due to differences in electric potential. Positively charged metal ions are adsorbed onto a negatively charged surface of a nanoparticle and vice versa. Examples of metal ions useful in this invention include, without limitation, copper ion ($Cu^{+2}$), silver ion ($Ag^{+1}$), gold ion ($Au^{+1}$ and $Au^{+3}$), iron (II) ion ($Fe^{+2}$), iron (III) ion ($Fe^{+3}$), permanganate ion ($MnO_4^{-1}$), and combinations thereof. These ions may be introduced through the aqueous addition of compounds like ferric chloride, copper chloride, silver nitrate, zinc chloride, magnesium oxide and so forth.

The nanoparticle may have a negative Zeta Potential and adsorb positively charged metal ions. One suitable nanoparticle has a negative Zeta Potential of about −1 to −50 millivolts and suitably about −1 to −20 millivolts and is a silica nanoparticle. Silica nanoparticles useful in this invention are available from Nissan Chemical Industries, Ltd., of Houston, Tex., USA, under the tradename SNOWTEX® and have a particle size range of 1-100 nanometers. The silica nanoparticle can be modified with a positively charged metal ion such as copper ions, silver ions, gold ions, iron ions, and combinations thereof.

Yet another useful nanoparticle has a positive Zeta Potential and adsorbs negatively charged metal ion complexes. One suitable nanoparticle has a positive first Zeta Potential of about 1 to 70 millivolts and suitably about 10 to 40 millivolts and may be an alumina nanoparticle. Alumina nanoparticles are available from Nissan Chemical Industries, Ltd., under the tradename ALUMINASOL®, and have a size range of about 1-300 nanometers. The alumina nanoparticle can adsorb negatively charged metal ions and metal ion complexes such as permanganate ions.

It is also possible to bond metal and silica particles to form a "coordinate" and/or "covalent bond." This may have a variety of benefits, such as reducing the likelihood that any of the metal will remain free during use (e.g., after washing). Strong adherence of the metal to the silica particles, further, also optimizes odor adsorption effectiveness. Numerous techniques may be utilized to form a stronger bond between the transition metal and silica particles. Silica sols, for example, are generally considered stable at a pH of greater than about 7, and particularly between a pH of 9-10. When dissolved in water, salts of transition metals are acidic (e.g., copper chloride has a pH of approximately 4.8). Thus, when such an acidic transition metal salt is mixed with a basic silica sol, the pH is lowered and the metal salt precipitates on the surface of the silica particles. This compromises the stability of the silica particles. Further, at lower pH values, the number of silanol groups present on the surface of the silica particles is reduced. Because the transition metal binds to these silanol groups, the capacity of the particles for the transition metal is lowered at lower pH values. In order to ameliorate the pH-lowering affect caused by the addition of an acidic transition metal salt (e.g., copper chloride), certain embodiments of the present invention employ selective control over the pH of the silica particles during mixing with the transition metal. The selective control over pH may be accomplished using any of a variety of well-known buffering systems known in the art.

The use of pH control in the modification of silica nanoparticles was demonstrated using a 10 weight percent suspension of SNOWTEX-OXS® nanoparticles having an unmodified particle size of 4 to 6 nm. The pH of the solution was adjusted to 8.7 and then added to a solution of copper chloride with high mixing shear (about 10,000 rpm). The pH, Zeta potential and particle size were monitored and when a positive Zeta potential was obtained the addition of copper chloride was stopped. The resulting copper modified nanoparticle had a particle size of about 43 nm and a surface area of about 500 square meters per gram.

Other techniques may also be utilized to further enhance the strength of the bonds formed between the transition metal and the silica particles. Coupling agents in an effective amount may be used to link the transition metal to the silica particle, for example. Such coupling agents may be employed with or without the pH adjustment discussed above. In some cases, an organofunctional silane coupling agent may be used to link the transition metal to the silica particles. Some examples of suitable organofunctional silane coupling agents that may be used include, but are not limited to, vinyltrichlorosilane, vinyltrimethoxysilane, vinyltriethoxysilane, vinylmethyldichlorosilane, vinylmethyldimethoxysilane, vinylmethyldiethoxysilane, 5-hexenyltrimethoxysilane, 3-glycidoxypropyltrimethoxysilane, 3-glycidoxypropyltriethoxysilane, 3-glycidoxypropylmethyldimethoxysilane, 3-glycidoxypropylmethyldiethoxysilane, 3-(meth)acryloxypropyltrimethoxysilane, 3-(meth)acryloxypropyltriethoxysilane, 3-(meth)acryloxypropylmethyldimethoxysilane, 3-(meth)acryloxypropylmethyldiethoxysilane, 4-vinylphenyltrimethoxysilane, 3-(4-vinylphenyl)propyltrimethoxysilane, 4-vinylphenylmethyltrimethoxysilane, 3-aminopropyltrimethoxysilane, 3-aminopropyltriethoxysilane, 3-aminopropylmethyldimethoxysilane, 3-aminopropylmethyldiethoxysilane, 3-(2-aminoethyl)aminopropyltrimethoxysilane, 3-mercaptopropyltrimethoxysilane, 3-mercaptopropyltriethoxysilane, 3-mercaptopropylmethyldimethoxy- silane, 3-mercaptopropylmethyldiethoxysilane, and partial hydrolyzates thereof. Of these coupling agents, organofunctional alkoxysilanes, and particularly aminofunctional alkoxysilanes (e.g., 3-aminopropyltriethyoxysilane), are preferred.

Generally speaking, the silane coupling agents may be covalently linked to the silica particles through the silanol groups (Si—OH) present on the surface thereof. Specifically, the silicon atom of the silane coupling agent may form a covalent bond with the oxygen of the silanol group. Once the silane coupling agent is covalently linked to the silica particles, the organofunctional group may form a coordinate bond with the transition metal. Copper, for example, may form a coordinate bond with different amino groups present on aminopropyltriethoxysilane coupling agents.

The addition of a metal ion adsorbed onto the surface of a nanoparticle provides an active site for capturing and neutralizing gases and odorous compounds. In addition, modified nanoparticles still have a large surface area that is useful in absorbing other odorous compounds. The metal ion active sites of the modified nanoparticles are particularly useful in removing odorous compound such as mercaptans, ammonia, amines, and mono- and di-sulfides. Other odorous compounds such as aliphatic ketones, carboxylic acids, aliphatic aldehydes, and aliphatic terpenoids can be removed by adsorption onto the large surface area of the modified nanoparticles. Modified nanoparticles are useful in removing odors caused by sulfides, disulfides, trisulfides, thiols, mercaptans, ammonia, amines, isovaleric acid, acetic acid, propionic acid, hexanal, heptanal, 2-butanone, 2-pentanone, 4-heptanone, and combinations thereof. Modified nanoparticles can also remove gases such as ethylene gas, carvone, dienals, and terpenoids.

More than one type of metal ion can be coated on a nanoparticle. This has an advantage in that certain metal ions may be more effective at removing specific gases and/or odorous compounds than other metal ions. More than one type of metal ion may be adsorbed onto a nanoparticle for more effectively removing more than one type of gaseous compound or odorous compound from a medium or for removing at least one gaseous compound and at least one odorous compound from a medium. The use of two or more different modified nanoparticles in combination can remove numerous odorous compounds. Modified silica nanoparticles, for example, are useful for removing sulphur and amine odors and modified magnesium oxide nanoparticles are useful in removing carboxylic acid odors. Combining modified nanoparticles allows for removal of a broader range of odors.

The odor removing ability of materials made according to the invention may be measured using a test for thiol odor removal using the GC headspace procedure with ethyl mercaptan (1 µl) as the odorant. This test uses a gas chromatography column, for example, a model DB-624:30 m, 0.25 mm ID, 1.4 micron film, catalog number 122-1334, serial number 8847844, from J&W Scientific, Inc. of Folsom, Calif., USA. The GC unit was Agilent Technologies 5890 GC with 7694 headspace analyzer with flame ionization detector. The headspace parameters were: oven temperature 37° C., loop temperature 85° C., transfer line temperature 90° C., GC cycle time 10 min., vial equalization time 10 min., pressurization time 0.2 min, loop fill time 0.2 min, injection time 0.3 min. The gas chromatographic parameters were: oven temperature 35° C. for five min., inlet temperature 105° C., detector temperature 225° C., and run time 5 minutes. Samples were weighted and place into the headspace vials without touching the bottom of the vial. The ethyl mercaptan was placed into the bottom of the vial using a microliter syringe. The vial was immediately crimped to seal in the gases. The amounts of odor for 20-200 percent odor removal by the sample were adjusted by dilution with hexane. The samples were prepared 10-60 minutes before running. Standard samples using the same amount of odor were run without a sample in the vial. Percent removal of odor was calculated by subtracting the area of the odor remaining from the total odor area and dividing by the total odor area. Gas chromatographic analysis indicated that the thiol binding capability of the basesheet was not diminished significantly by the addition of the polymeric binder.

Modified nanoparticles are made by mixing nanoparticles with solutions containing metal ions. Such solutions are generally made by dissolving metallic compounds into a solvent resulting in free metal ions in the solution. The metal ions are drawn to and adsorbed onto the nanoparticles due to the electric potential differences. The Zeta Potential of a nanoparticle changes after the adsorption of metal ions and so the Zeta Potential can be used to monitor the adsorption of metal ions onto the nanoparticle.

Further discussion of the modification of nanoparticles may be found in U.S. patent application Ser. No. 10/137,052, filed on Apr. 30, 2002, which is incorporated by reference.

The extrudates containing the odor absorbing, nanoparticles of this invention may be made in a number of ways. The modified nanoparticles may, for example, be added to the fillers used in extrudate production prior to or immediately after the coating of the fillers with a fatty acid.

It has been found that most fillers are not hydrophobic prior to the addition of fatty acid, but that fillers are hydrophobic after treatment with fatty acid. Prior to fatty acid treatment, therefore, an aqueous mixture of nanoparticles and metal ions, mixed with filler, can be used to add the nanoparticles to the filler. The aqueous mixture may be made by adding sufficient metal ion to produce a solution having between 0.05 and 25 weight percent metal ion, more desirably between about 0.25 and 10 weight percent and more desirably about 1 weight percent metal ion. Nanoparticles in an amount sufficient to produce a solution of between 0.5 and 40 weight percent, more desirably between about 5 and 30 weight percent and more desirably between about 15 and 25 weight percent are then added to this solution. Lastly, the filler is added in an amount sufficient to produce a mixture that may be stirred. The modification of the nanoparticles and their addition to the filler surface takes place very rapidly upon mixing. After the modified nanoparticle addition the filler may be treated with fatty acid in the conventional way and further processed for use.

If, instead of adding the modified nanoparticles to the filler particles before fatty acid treatment, it is desired to do so after the addition of fatty acid to the filler, the addition of nanoparticles to the filler becomes more difficult. In this case the hydrophobicity of the filler particle surface must be overcome. It is believed, though the inventors do not wish to be bound by this belief, that ultrasonic energy introduced to an aqueous solution causes a change in the temperature and pressure of the solution in the immediate area of the horn. This change in temperature and pressure is believed to allow the aqueous solution to wet a usually hydrophobic surface and to cause suspended or dissolved materials to be deposited onto the surface. An aqueous mixture of nanoparticles, metal ions and fatty acid-treated filler in the amounts given above, for example, may be placed near the submerged horn of an ultrasonic machine. Upon the addition of ultrasonic energy, the hydrophobicity of the fatty acid treated filler is overcome and nanoparticles containing metal ions are deposited onto the surface of the filler particles. The finished filler may be dried and processed for use in extrudate production.

Manufactures of suitable ultrasonic equipment include Branson Ultrasonic Corporation, Applied Technology Group, Danbury, Conn., USA, UE Systems Inc. of Elmsford, N.Y., USA, Mecasonic SA of Chatou, France, and Dukane Corporation, St. Charles, Ill., USA.

Commercial extrudate production generally uses pre-prepared pellets of polymer to which have been added filler in a high amount, for example around 75 weight percent. The proper amount of filler/polymer pellets are added to pure polymer pellets to yield an extrudate with the desired amount of filler. Commercial breathable films, for example, generally have about 60 weight percent filler. Once the nanoparticle treated filler has been compounded into a polymer pellet it may be used in any conventional extrusion technology as currently done with the filler/polymer pellets.

Figure 5:
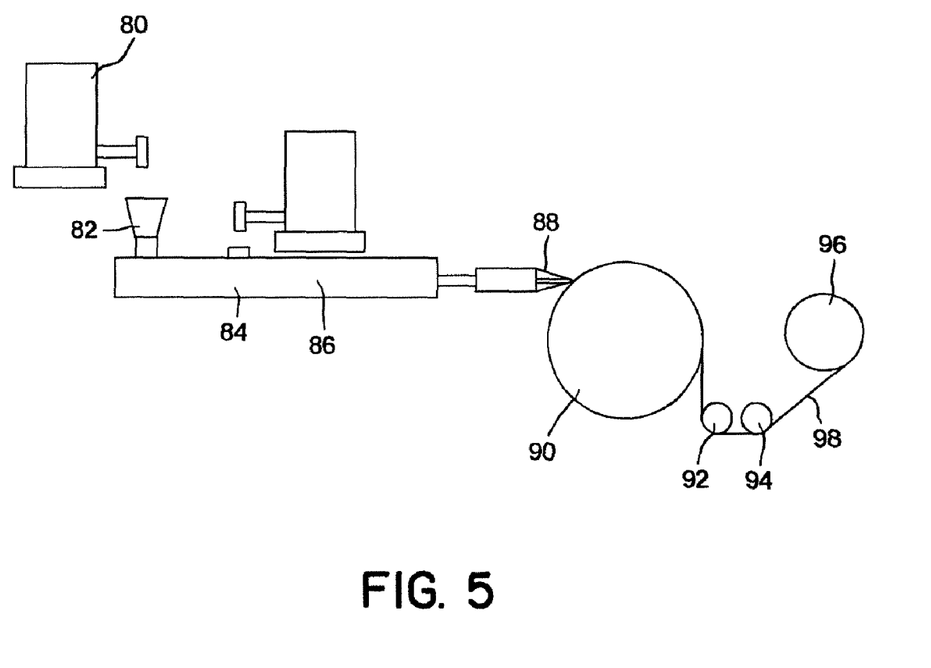
FIG. 5 shows a schematic diagram of a process for making a film.

FIG. 5 shows a schematic diagram of a process for making a film. The polymers from which the film will be made are mixed together with each other and placed in the hopper 80. The polymer is metered from the hopper 80 into the receiving end 82 of the extruder 84. The polymer is moved through the extruder 84 by twin screws (not shown) that cause intimate mixing, heating and pressurization of the polymer. In this FIG. 5, filler is added at zone 4 86 of the extruder 84, though it may be added at other points consistent with the desires of the operator. The polymer and filler mixture continues to be heated, mixed and pressurized as it continues through the extruder 84 to the die 88 where it is discharged from the extruder 84. The extruded film 98 is collected on a chill roll 90 that cools the still warm extrudate. The film 98 then is passed around stretching rolls 92, 94 and collected on yet another roll 96. The film may alternatively be collected on a storage roll without stretching and stretched at a later time.

Breathable films and laminates thereof having odor absorbing, nanoparticles are suitable for use in many commercial articles like, for example, personal care products, trash and storage bags, curtains, wallpaper, sheets and towels, and in medical applications like face masks and drapes. Personal care product means diapers, training pants, absorbent underpants, adult incontinence products, and feminine hygiene products.

Figure 6:
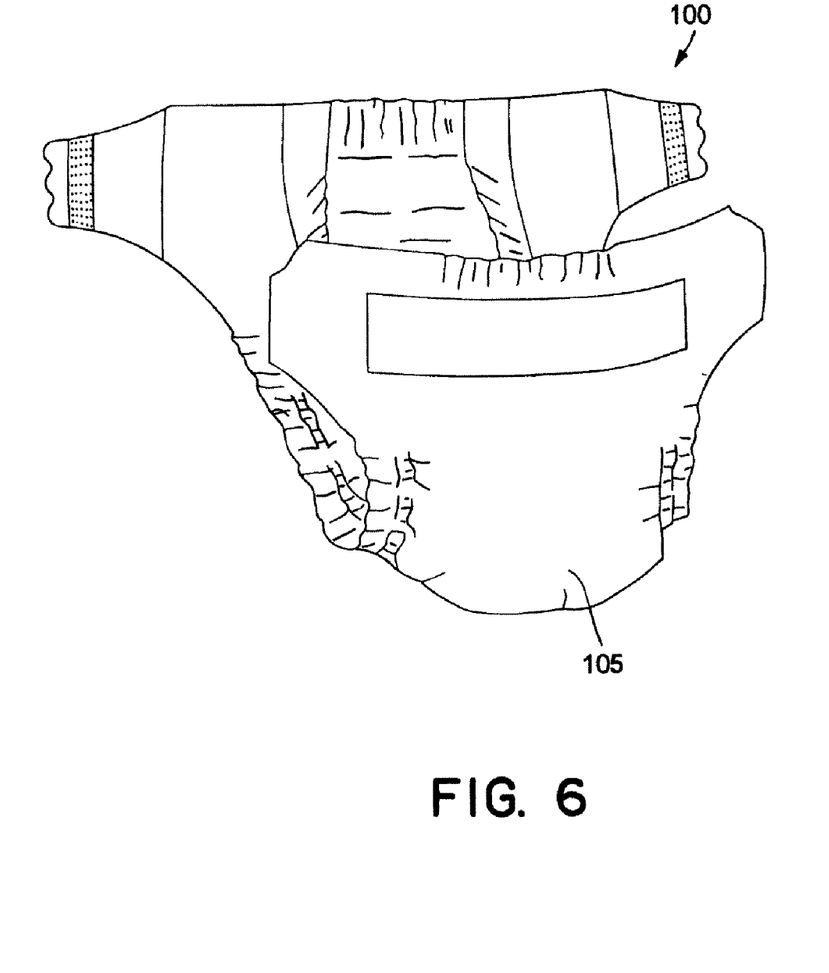
FIG. 6 is a drawing of a diaper.
Figure 7:
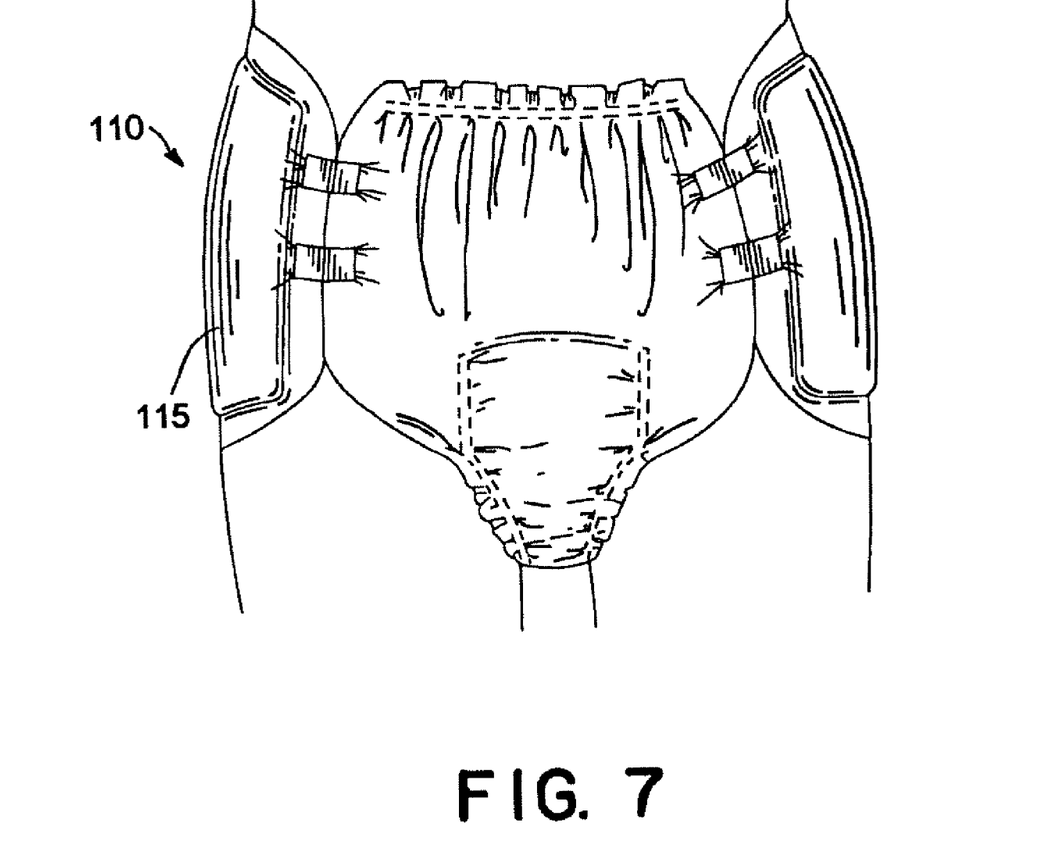
FIG. 7 is a drawing of an adult incontinence product.

Personal care products generally include an outer cover that is typically formed of a thin thermoplastic film, nonwoven fabric or multilayer laminate that is substantially impermeable to liquid. The outer cover functions to prevent body exudates contained in an absorbent structure from wetting or soiling the wearer's clothing, bedding, or other materials contacting the diaper. The outer cover may be, for example, a polyethylene film having an initial thickness of from about 0.5 mil (0.012 millimeter) to about 5.0 mil (0.12 millimeter). The polymer film outer cover may be embossed and/or matte finished, providing a more aesthetically pleasing appearance. Other alternative constructions for outer cover include woven or nonwoven webs that have been constructed or treated to impart the desired level of liquid impermeability, or laminates formed of a woven or nonwoven fabric and thermoplastic film. The outer cover is desirably breathable yet substantially impermeable to liquid. FIG. 6 is a drawing of a diaper 100 showing the outer cover 105. FIG. 7 is a drawing of an adult incontinence article 110 showing the outer cover 115 which may be a breathable film according to the invention.

In another aspect of this invention, the extrudate having the modified high surface area particles is used to absorb gases that plants produce to ripen fruit. Ethylene gas is produced by plants as a hormone to aid fruit ripening. Removing ethylene gas as it is produced can slow and control the fruit ripening process. Permanganate ion modified alumina nanoparticles are useful in removing ethylene gas and such nanoparticles may be added to breathable films, nonwoven fabrics or multilayer laminates using the methods described above. The fabric can then be used in packaging and storing fruit to inhibit ripening by removing ethylene gas.

The following examples aid in the understanding of the invention.

Example 1

A solution of 1 weight percent copper chloride ($CuCl_2$) was made by adding 3 gm of copper chloride to 300 ml distilled, deionized water, stirring until dissolution without heat addition. An amount of 162 gm of this solution was mixed with 375 gm of 20% SNOWTEX-AK® nanoparticles from Nissan Chemical Industries. This solution was diluted with 3 liters of distilled, deionized water. 1500 gm of calcium carbonate without stearic acid (from Omya Inc., Alpharetta, Ga., USA, a subsidiary of Omya AG of Germany) was added to the solution and the slurry thoroughly mixed and then dried. The resulting dried case was crushed and coated with stearic acid according to know procedures. A breathable film was made using this treated filler. The film had a copper concentration of 0.054 weight percent.

The film was made using a co-rotating 27 mm twin screw extruder made by Leistriz Ag of Nurenburg, Germany with a throughput of 4 pounds (1.8 kg) per hour and a 6 inch (15.2 mm) film die. The temperature of the extruder was maintained at 200° C., the die at 200° C. and the melt at 221° C. The screw rotated at 270 rpm, the pressure at the 6 inch film die was 800 psi (5516 kPa), the chill roll rotated at a rate of 14.5 linear feet (442 cm) per minute and the winder rotated at a speed of 15 linear feet (457 cm) per minute. The polyethylene polymer was added to the hopper and the calcium carbonate was added to zone 4 of the extruder at the same weight rate and this 1:1 ratio was maintained throughout the test. The film was subsequently stretched by a factor of 4 at 70° C. at a rate of 10 inches (25.4 cm) per minute or 300 percent per minute, using a Blue-M Power-O-Matic 60 oven having movable grips that hold onto and stretch the film. Upon stretching the film developed micropores initiated by the calcium carbonate particles.

Example 2

A solution of 1 weight percent copper chloride ($CuCl_2$) was made by adding 3 gm of copper chloride to 300 ml distilled, deionized water, stirring until dissolution without heat addition. An amount of 107.5 gm of this solution was mixed with 50 gm of 20 weight percent SNOWTEX-AK® nanoparticles from Nissan Chemical Industries. This solution was diluted with 1 liter of distilled, deionized water. 500 gm of calcium carbonate conventionally treated with stearic acid and available from Omya Inc. was added to the solution. An ultrasonic horn was immersed in the solution within one half inch (1.25 cm) from the bottom of the container and short (0.5-3 seconds) bursts of sonic energy were applied. This was done for approximately 50 repetitions, with the container moved slightly each time so that all parts of the solution would be exposed to the sonic energy. The ultrasonic horn was a 2000 watt Branson 900lw bonder with a 0.5 by 6 inch (1.26 by 15.25 cm) horn and 1:1.5 booster, available from Branson Ultrasonic Corporation, Applied Technology Group, Danbury, Conn., USA.

Uniform wetting out of the stearic acid coated calcium carbonate was achieved as noted by the uniformity of color and opacity of the solid and liquid combination.

The solution was poured into a shallow pan and dried at 70-100° C. for about 48 hours. The dried material often formed a solid cake that could be crumbled apart and further ground to a fine powder. After grinding, this material was placed in a powder feed hopper and metered into an extruder along with polyethylene and a film produced as in Example 1.

Control

A control film, not an example of the invention, was a polyethylene film filled with 60 weight percent stearic acid coated calcium carbonate.

The odor removing capability of the films was measured by the GC headspace procedure given above, with ethyl mercaptan (EtSH) (2.4 µl) as the odorant. The WVTR in g/m²/day of the films was also measured. The results are shown in Table 1.

TABLE 1

| | WVTR | mg EtSH/g CuCl$_2$ |
|---|---|---|
| Control | 3936 | 0 |
| Example 1 | 774 | 3698 |
| Example 2 | 339 | 1662 |

As can be seen from the results in Table 1, the control film, though having a very high WVTR, removed no odor. The films of the invention had a lower WVTR due to a lower calcium carbonate content but had a significant amount of odor absorbed. It should be noted that the WVTR of the Examples is still considered quite high.

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention.

What is claimed is:

1. A breathable film comprising a thermoplastic polymer and a filler blended with silica nanoparticles, wherein said silica nanoparticles have a diameter of about 500 nanometers or less and a negative first Zeta Potential from about −1 to about −50 millivolts as measured in an aqueous suspension, said silica nanoparticles being modified with a metal ion to form modified silica nanoparticles, said metal ion selected from the group consisting of copper ion, silver ion, gold ion, iron ion, and combinations thereof, wherein said modified silica nanoparticles comprise a second Zeta Potential being at least about 5.0 millivolts higher than said negative first Zeta Potential.

2. The breathable film of claim 1, wherein the filler comprises at least 35% by weight of said breathable film.

3. The breathable film of claim 1, wherein the filler comprises from about 45% to about 65% by weight of said breathable film.

4. The breathable film of claim 1, wherein the filler has an average particle size of about 0.1 microns to about 10 microns.

5. The breathable film of claim 1, wherein the filler is coated with a fatty acid.

6. The breathable film of claim 1, wherein the filler is selected from the group consisting of calcium carbonate, clays, silica, alumina, barium sulfate, talc, magnesium sulfate, titanium dioxide, zeolites, aluminum sulfate, cellulose powders, diatomaceous earth, gypsum, magnesium sulfate, magnesium carbonate, barium carbonate, kaolin, mica, carbon, magnesium oxide, aluminum hydroxide, pulp powder, wood powder, cellulose derivatives, polymeric particles, chitin, chitin derivatives, and combinations thereof.

7. The breathable film of claim 1, wherein the filler comprises calcium carbonate.

8. The breathable film of claim 1, wherein said negative first Zeta Potential is from about −1 to about −20 millivolts.

9. The breathable film of claim 1, wherein said film has a WVTR of at least 300 g/m²/day.

10. The breathable film of claim 1, wherein said film has a WVTR of at least 500 g/m²/day.

11. The breathable film of claim 1, wherein the surface area of said silica nanoparticles is at least 100 m²/g.

12. The breathable film of claim 1, wherein the surface area of said silica nanoparticles is at least 200 m²/g.

13. The breathable film of claim 1, wherein the surface area of said silica nanoparticles is at least 500 m²/g.

14. The breathable film of claim 1, wherein the thermoplastic polymer is a polyolefin.

15. The breathable film of claim 1, wherein said metal ions are adsorbed onto said silica nanoparticles to form said modified silica nanoparticles.

16. The breathable film of claim 1, wherein said metal ions are bonded to said silica nanoparticles via coordinate bonds, covalent bonds, or mixtures thereof to form said modified nanoparticles.

17. The breathable film of claim 1, wherein said metal ions are coupled to said silica nanoparticles with an organofunctional silane to form said modified silica nanoparticles.

18. A breathable film comprising a thermoplastic polymer and a filler blended with nanoparticles, wherein said nanoparticles have a diameter of about 500 nanometers or less and a positive first Zeta Potential from about 1 to about 70 millivolts, said nanoparticles being modified with a metal ion to form modified nanoparticles, wherein said modified nanoparticles comprise a second Zeta Potential being at least about 5.0 millivolts lower than said positive first Zeta Potential.

19. The breathable film of claim 18, wherein said nanoparticles are alumina nanoparticles.

20. The breathable film of claim 18, wherein said metal ion is selected from the group consisting of permanganate ion, chlorite ion, persulfate ion, and combinations thereof.

21. The breathable film of claim 20, wherein said metal ion is permanganate ion.

22. The breathable film of claim 18, wherein said metal ions are adsorbed onto said nanoparticles to form said modified nanoparticles.

23. The breathable film of claim 18, wherein said metal ions are bonded to said nanoparticles via coordinate bonds, covalent bonds, or mixtures thereof to form said modified nanoparticles.

24. The breathable film of claim 18, wherein said metal ions are coupled to said nanoparticles with an organofunctional silane to form said modified nanoparticles.

25. A personal care product comprising an outer cover, said outer cover comprising a breathable film and having a WVTR about 500 g/m²/day or greater, said breathable film comprising a thermoplastic polymer and a filler blended with nanoparticles, wherein said nanoparticles have a diameter of about 500 nanometers or less and selected from the group consisting of silica, alumina, and combinations thereof, wherein said nanoparticles are modified with a metal ion to form modified nanoparticles.

26. The personal care product of claim 25 further comprising a nonwoven fabric laminated to said breathable film.

27. The personal care product of claim 25, wherein the personal care product is a diaper.

28. The personal care product of claim 25, wherein the personal care product is an adult incontinence product.

29. The breathable film of claim 1, wherein said breathable film is formed by coextruding said thermoplastic polymer with said blend of filler and silica nanoparticles.

* * * * *